(12) United States Patent
Nuernberger et al.

(10) Patent No.: US 9,119,922 B2
(45) Date of Patent: Sep. 1, 2015

(54) APPARATUS AND METHOD FOR IDENTIFYING A TUBING SYSTEM FOR AN EXTRACORPOREAL BLOOD TREATMENT DEVICE

(75) Inventors: Thomas Nuernberger, Burkardroth (DE); Peter Kloeffel, Nuedlingen (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 763 days.

(21) Appl. No.: 13/320,783

(22) PCT Filed: May 15, 2010

(86) PCT No.: PCT/EP2010/002990
§ 371 (c)(1),
(2), (4) Date: Nov. 16, 2011

(87) PCT Pub. No.: WO2010/133319
PCT Pub. Date: Nov. 25, 2010

(65) Prior Publication Data
US 2012/0061320 A1 Mar. 15, 2012

(30) Foreign Application Priority Data
May 19, 2009 (DE) .......................... 10 2009 021 995

(51) Int. Cl.
*B01D 21/24* (2006.01)
*B01D 24/38* (2006.01)
*A61M 1/34* (2006.01)

(52) U.S. Cl.
CPC .............. *A61M 1/342* (2013.01); *A61M 1/3434* (2013.01); *A61M 2205/3334* (2013.01); *A61M 2205/6018* (2013.01)

(58) Field of Classification Search
CPC .............. A61M 1/342; A61M 1/3434; A61M 2205/3334; A61M 2205/6018

USPC .................................................. 210/103, 646
See application file for complete search history.

(56) References Cited

U.S. PATENT DOCUMENTS 5,047,014 A 9/1991 Mosebach et al.
5,049,047 A 9/1991 Polaschegg et al.
(Continued)

FOREIGN PATENT DOCUMENTS

DE 38 42 404 6/1990
DE 39 12 405 10/1990
(Continued)

OTHER PUBLICATIONS

International Preliminary Report on Patentability for PCT/EP2010/002990 mailed Nov. 29, 2011.
(Continued)

*Primary Examiner* — Dirk Bass
(74) *Attorney, Agent, or Firm* — Kenyon & Kenyon LLP

(57) ABSTRACT

The invention relates to an apparatus for extracorporeal blood treatment, comprising a device for detecting a tubing system to be placed in the blood treatment apparatus and a method for detecting a tubing system to be placed in an extracorporeal blood treatment apparatus. The tubing system is detected on the basis of the dependency of the flow rate Q, at which the fluid is delivered by at least one pump of the extracorporeal blood treatment apparatus in a tubing section of the tubing system, on the speed n at which the at least one pump is operated, and on the inner diameter d of the tube of the tubing section. Because the dependency of the flow rate on the pump speed and the tube cross section is known, a conclusion can be drawn as to whether a particular tubing system has been placed in the extracorporeal blood treatment apparatus.

13 Claims, 3 Drawing Sheets

(56) References Cited

U.S. PATENT DOCUMENTS 5,644,402 A 7/1997 Chevallet
6,164,921 A 12/2000 Moubayed et al.

FOREIGN PATENT DOCUMENTS

| DE | 699 15 869 | 3/2005 |
| EP | 0 238 809 A2 | 9/1987 |
| EP | 0 467 805 A1 | 1/1992 |
| EP | 1 112 099 B1 | 11/2006 |

OTHER PUBLICATIONS

PCT International Search Report and Written Opinion from PCT/EP2010/002990 mailed Sep. 1, 2010.

APPARATUS AND METHOD FOR IDENTIFYING A TUBING SYSTEM FOR AN EXTRACORPOREAL BLOOD TREATMENT DEVICE

CROSS REFERENCE TO RELATED APPLICATIONS

This is a 371 national phase application of PCT/EP2010/002990 filed May 15, 2010, claiming priority to German Patent Application No. 10 2009 021 995.1 filed May 19, 2009.

FIELD OF INVENTION

The invention relates to an apparatus for extracorporeal blood treatment with a device for recognizing a tubular line system to be inserted into the blood treatment apparatus. Moreover, the invention relates to a method for recognizing a tubular line system to be inserted into an extracorporeal blood treatment apparatus.

BACKGROUND OF THE INVENTION

Various methods for extracorporeal blood treatment are known. In the case of hemodialysis (HD), the blood of the patient is cleaned in an extracorporeal blood circuit which comprises a dialyzer. The dialyzer has a blood chamber and a dialysis fluid chamber which are separated by a semipermeable membrane.

Whereas the dialysis fluid flows through the dialysis fluid chamber during hemodialysis (HD), with certain substances being transported through the membrane on account of the diffusion between the dialysis fluid and the blood, the dialysis fluid does not flow through the dialysis fluid chamber of the dialyzer during hemofiltration (HF). In hemofiltration (HF), certain substances are effectively removed through the membrane of the filter due to convection. Hemodiafiltration (HDF) is a combination of the two methods.

It is widely known to replace part of the fluid, taken from the patient via the membrane of the dialyzer or the filter, by a sterile substitution fluid which is supplied to the extracorporeal blood circuit either upstream or downstream of the dialyzer. Apparatuses for extracorporeal blood treatment are known, in which apparatuses the dialysis fluid is produced online from fresh water and concentrates and the substitution fluid is produced online from dialysis fluid.

Different tubular line systems, which are designed for single use and are inserted into the blood treatment apparatus, are used for the various extracorporeal blood treatments. By way of example, tubular lines of tubular line systems whose internal diameters differ from one another are known for treating adults or children.

The extracorporeal blood treatment apparatuses comprise a number of pumps by means of which the blood of the patient, the substitution fluid or rinsing fluids are pumped through the tubular lines of the tubular line systems.

Peristaltic pumps are used to pump fluids in the extracorporeal blood treatment apparatuses, in which at least one constriction or occlusion site moves along the elastic tube serving as pump space. In the most commonly used design of peristaltic tube pumps, the elastic tube is completely closed off at the constriction or occlusion site. It is for this reason that these pumps are also known as occluding tube pumps. The most commonly used occluding tube pump is a roller pump, into which a section of the tubular line of the tubular line system is inserted.

SUMMARY OF THE INVENTION

The invention is based on the object of providing an apparatus for extracorporeal blood treatment which permits the recognition of the tubular line system to be inserted into the extracorporeal blood treatment apparatus. Moreover, it is an object of the invention to specify a method by means of which the tubular line system to be inserted into the extracorporeal blood treatment apparatus can be recognized.

Recognizing the tubular line system to be inserted into the extracorporeal blood treatment apparatus offers different possibilities for simplifying the extracorporeal blood treatment apparatus and increasing the safety of the extracorporeal blood treatment. Once the tubular line system has been recognized, it is possible to undertake an intervention in the machine control. By way of example, it is possible to only permit a certain blood treatment, for example only hemodialysis (HD) but not hemofiltration (HF) or hemodiafiltration (HDF), with the blood treatment apparatus after a certain tubular line system has been inserted. However, it is also possible to make certain specifications for the blood treatment after the tubular line system has been recognized. It is also possible for there to be a check as to whether the correct tubular line system for the predetermined blood treatment has been inserted once the tubular line system has been recognized, for example, it is possible to distinguish between a tubular line system for the treatment of an adult or a child.

In the apparatus according to the invention and the method according to the invention, the recognition of the tubular line system relies on the basic principle of the flow rate, with which the fluid is pumped in a tubular line section of the tubular line system by at least one pump of the extracorporeal blood treatment apparatus, depending on the rotational speed, at which the at least one pump is operated, and the internal diameter of the tubular line of the tubular line section. Since the dependence of the flow rate on the pump rotational speed and tubular line cross section is known, it can be deduced whether a certain tubular line system is inserted into the extracorporeal blood treatment device. Thus, the cross section of the tubular line of a tubular line section of the tubular line system is used as an indicator for recognizing the tubular line system.

The apparatus according to the invention and the method according to the invention afford the possibility of distinguishing between the tubular line for the treatment of an adult or a child since the two tubular line systems have different tubular line cross sections. However, it is also possible to provide only one tubular line section of a tubular line system with a certain cross section which differs from the cross section of another tubular line system. This makes it possible to use the apparatus according to the invention or the method according to the invention to distinguish between the two tubular line systems. In the process, it is possible to provide a tubular line section which is not used for the actual blood treatment but only for example for rinsing, with a different internal diameter, in particular with a reduced internal diameter. However, the tubular line section which supplies substitution fluid but not the patient's blood can also be used to characterize the tubular line system by a changed cross section.

In the case of known extracorporeal blood treatment apparatuses, two pumps, arranged one behind the other, are generally used to pump fluid during the rinsing process. The first pump pumps fluid in a first tubular line section and the second pump pumps fluid in a second tubular line section of the tubular line system. Generally, the pumps are occluding tube pumps into which the first and second tubular line sections are inserted. Both tubular line sections can have the same internal diameter. However, in order to characterize a certain tubular line system, one of the two tubular line sections can also have a larger or a smaller cross section.

A preferred embodiment of the invention assumes that under the condition of the first and the second pump pumping fluid at the same flow rate (feed rate), the pumps have the same rotational speeds in the case of equal cross sections of the two tubular line sections and the pumps have different rotational speeds in the case of different cross sections. In the preferred embodiment, the pressure is measured in the tubular line between the first and the second pump. In the process, the pump rotational speeds are set so that the pressure during the operation of the pumps remains constant for at least a predetermined time interval. The relation of the rotational speeds between the first and the second pump allows a deduction to be made as to whether the internal diameters of the tubular lines are the same or different. The relation of the rotational speeds also affords the possibility of calculating the internal diameter of the tubular line of one of the two tubular line sections if the internal diameter of the tubular line of the respective other tubular line section is known.

When a constant pressure is mentioned in this context, pressure pulses that are superposed on the substantially constant pressure signal should, however, be taken into account in practice. Hence an oscillating pressure signal is measured in practice. These pressure pulses can be traced back to the fact that the blood pump generally is a roller pump, the rollers of which occlude the tubular line. The pressure pulses are generated as a result of the tubular line occluding when the rollers are lifted from the tubular line or placed thereon.

In practice, the pressure pulses must not be taken into account in the evaluation. To this end, it is possible, for example, to calculate a mean pressure, which should be constant, over a predetermined time interval. The evaluation unit can be used to calculate the mean value. However, instead of forming a mean value, it is also possible to predetermine upper and/or lower thresholds, with a constant pressure being assumed if the pressure signal moves in the predetermined threshold window. However, it also possible, for example, to remove the measured pressure signal from the pressure pulses. By way of example, this is possible by filtering the measured values, in particular by subjecting the measured values to a low-pass filter because the pressure pulses occur periodically.

An alternative embodiment of the invention provides for recognizing the tubular line system from the cross section of the tubular line by measuring the flow rate of the fluid which is pumped through a tubular line section of the tubular line system with a pump of the extracorporeal blood treatment apparatus. The pump is operated at a rotational speed at which, under the assumption of the tubular line having a certain internal diameter, a certain flow rate results. If the assumed flow rate and the measured flow rate are identical, it is deduced that the internal diameter of the tubular line used is equal to the internal diameter of the assumed tubular line. Using this, it can be assumed that the correct tubular line is inserted into the blood treatment apparatus.

Since in practice it can be assumed that the flow rate cannot be calculated or measured exactly, certain deviations are tolerated. It is for this reason that the value of the difference between the rotational speeds or flow rates, or their quotient, is preferably compared to a reference value.

The apparatus according to the invention advantageously makes it possible to recognize the tubular line system using components which are generally present in any case in known blood treatment apparatuses. By way of example, pumps for pumping blood or substitution fluid are available in any case. A unit for measuring the pressure in the tubular line is also present in known blood treatments. Known blood treatment apparatuses in general also comprise a unit by means of which the flow rate of the fluid can be determined. By way of example, a balancing unit which is used in blood treatment apparatuses can be used to measure the flow rate.

BRIEF DESCRIPTION OF THE DRAWINGS

In the following text, exemplary embodiments of the invention are explained in more detail with reference to the drawings, in which.

DETAILED DESCRIPTION OF THE DRAWINGS

Figure 1:
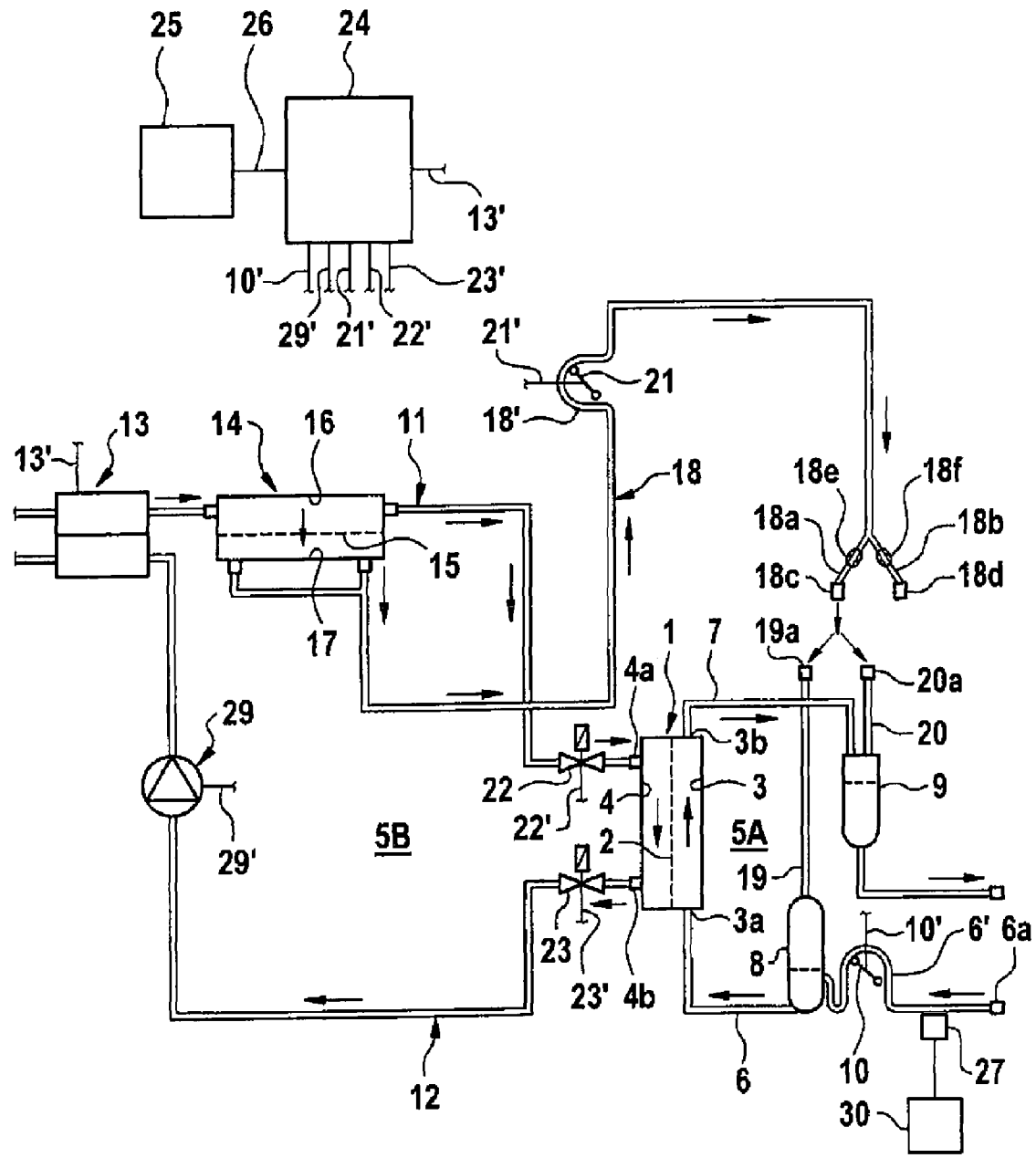
FIG. 1 shows the essential components of an apparatus for extracorporeal blood treatment with a device for recognizing the tubular line system, an extracorporeal blood treatment being carried out by the extracorporeal blood treatment apparatus.

FIG. 1 shows a simplified schematic illustration of the essential components of an extracorporeal blood treatment apparatus, in particular a hemo(dia)filtration apparatus, which has a device for recognizing the tubular line system inserted or to be inserted into the blood treatment apparatus.

The hemo(dia)filtration apparatus has a dialyzer 1 which is separated into a first chamber 3, through which blood flows, and a second chamber 4, through which dialysis fluid flows, by a semipermeable membrane 2. The first chamber 3 is connected to an extracorporeal blood circuit 5A, while the second chamber 4 is connected to the fluid system 5B of the hemo(dia)filtration apparatus. When a dialyzer is discussed in the following text, it is also understood to mean a filter.

The extracorporeal blood circuit 5A comprises an arterial blood line 6 which leads to the inlet $3a$ of the blood chamber 3, and a venous blood line 7 which starts at the outlet $3b$ of the blood chamber 3 of the dialyzer 1. To eliminate air bubbles, the present exemplary embodiment has an arterial drip chamber 8 connected to the arterial blood line 6 and a venous drip chamber 9 connected to the venous blood line 7. The arterial and venous blood lines 6, 7 are two separate tubular line sections 6, 7 of a tubular line system designed for single use. In the present exemplary embodiment, both tubular line sections 6, 7 are connected to the inlet and outlet $3a$, $3b$ of the dialysis fluid chamber 3 via connectors (not illustrated). The tubular lines of the two tubular line sections 6, 7 have the same internal diameter $d_B$. A line section 6' of the arterial tubular line section 6 is inserted into an occluding pump 10, in particular a roller pump, which pumps the blood of the patient in the extracorporeal blood circuit 5A.

The fluid system 5B comprises a dialysis fluid supply line 11 which leads to the inlet $4a$ of the dialysis fluid chamber 4, and a dialysis fluid discharge line 12 which starts at the outlet $4b$ of the dialysis fluid chamber 4 of the dialyzer 1. Fresh dialysis fluid from a dialysis fluid source (not illustrated) streams into the dialysis fluid chamber via the dialysis fluid supply line 11, while used dialysis fluid is discharged from the dialysis fluid chamber to an outflow (not illustrated) via the dialysis fluid discharge line 12. The dialysis fluid is pumped by a dialysis fluid pump 29 which is arranged in the dialysis fluid discharge line 12. A balancing unit 13, which is firstly connected to the dialysis fluid supply line 11 and secondly connected to the dialysis fluid discharge line 12, is used to balance fresh and used dialysis fluid so that both inflowing and outflowing dialysis fluid flows through the balancing chambers of the balancing unit.

A sterile substitution fluid can be supplied to the extracorporeal blood circuit 5A during the blood treatment. The sterile substitution fluid is obtained from the dialysis fluid of the dialysis fluid system 5B. A sterile filter 14 which is subdivided into a first chamber 16 and a second chamber 17 by a membrane 15 is used to obtain the sterile substitution fluid. The first chamber 16 is connected to the dialysis fluid supply line 11, and a substitution fluid line 18 starts from the second chamber 17 and leads to the extracorporeal blood circuit 5A.

At its ends, the substitution fluid line 18 has two line sections 18a, 18b to which in each case one connector 18c, 18d is connected. Using the two connectors 18c, 18d, the substitution fluid line 18 can be connected to a connecting line 19, leading to the arterial drip chamber 8, or to a connecting line 20, leading to the venous drip chamber 9. It is for this reason that the connecting lines 19, 20 have corresponding connecting pieces 19a, 20a. On the line sections 18a, 18b, there are tube clamps 18e, 18f by means of which a fluid connection can optionally be made to the arterial and/or venous drip chamber 8, 9.

The substitution fluid line 18 is once again a separate tubular line section of the tubular system. A line section 18' of the tubular line section 18 is inserted into a substituate pump 21, in particular a roller pump, by means of which the substitution fluid is pumped. The tubular line section 18 for supplying the substitution fluid has an internal diameter $d_A$, which can be equal to the internal diameter $d_B$ of the tubular line sections of the arterial and venous blood lines 6, 7, or which can differ from the internal diameter $d_B$ of the two tubular line sections 6, 7.

In order to clamp off the dialyzer 1, provision is made for a locking organ 22 in the dialysis fluid supply line 11 and for a locking organ 23 in the dialysis fluid discharge line 12. The blood treatment apparatus can additionally comprise further components, such as additional sterile filters, locking organs, connectors or the like; however these are not illustrated for the purpose of improved clarity.

The blood treatment apparatus is controlled using a central control unit 24 which is connected to the arterial blood pump 10, the dialysis fluid pump 29, the substituate pump 21 and the locking organs 22 and 23 via control lines 10', 29', 21', 22', 23'. The central control unit 24 can switch individual pumps on and off, and can set the rotational speeds thereof.

The extracorporeal blood treatment apparatus has a device for recognizing the tubular line system inserted or to be inserted into the blood treatment apparatus, which device comprises the tubular line sections 6, 7, 18 in the present exemplary embodiment. The device for recognizing the tubular line system has an evaluation unit 25 which is connected to the central control unit 24 of the blood treatment apparatus via a data line 26. However, the evaluation unit 25 can also be a component of the central control unit 24 because the components required for implementing the evaluation unit, e.g. a microprocessor or the like, are already available in the central control unit. In addition to the evaluation unit 25, the device for recognizing the tubular line system has a pressure measuring unit 27, which measures the pressure in the arterial blood line 6 upstream of the blood pump 10 using a pressure sensor 27.

Figure 2:
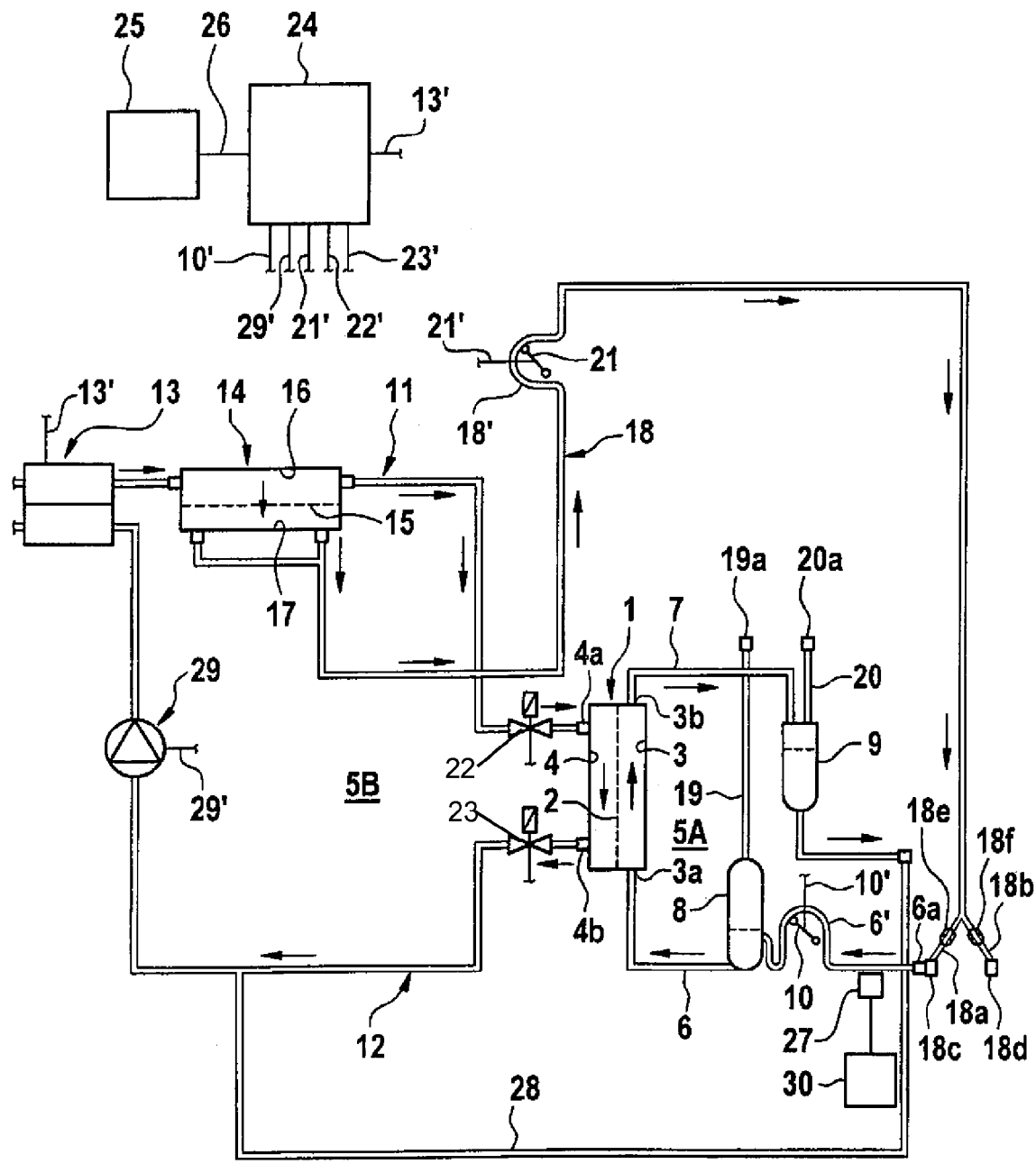
FIG. 2 shows the extracorporeal blood treatment apparatus from FIG. 1, the blood treatment apparatus being rinsed.

The tubular line system 6, 7, 18 is recognized during a rinsing phase which precedes the blood treatment. FIG. 2 shows the blood treatment apparatus from FIG. 1 during the rinsing phase. In order to rinse the blood treatment apparatus, the substitution fluid line 18 is not connected to the connecting lines 19 and 20 respectively leading to the drip chambers 8 and 9, but to the end of the arterial blood line 6. To this end, the connector 18c is connected to a fitting connector 6a which is provided at the end of the blood line 6. Furthermore, the tube clamp 18e is opened and the tube clamp 18f is closed. Moreover, the locking organs 22 and 23 at the inlet and outlet 4a, 4b of the dialysis fluid chamber 4 of the dialyzer 1 are closed. It follows that the rinsing fluid can flow into the sterile filter 14 via the dialysis fluid supply line 11 and into the blood chamber 3 of the dialyzer 1 via the substitution fluid line 18 and the arterial blood line 6. From the blood chamber 3, the rinsing fluid flows into the venous blood line 7 which, during the rinsing phase, is connected to the dialysis discharge line 12 via an only indicated line path 28.

The present exemplary embodiment assumes that the internal diameter $d_A$ of the tubular line section of the substitution fluid line 18 differs from the internal diameter $d_B$ of the two tubular line sections of the arterial and venous blood lines 6, 7. In this case, the internal diameter $d_B$ is greater than the internal diameter $d_A$. By way of example, the internal diameter $d_B$ is 8 mm, and the internal diameter $d_A$ is 4 mm. The tubular line system 6, 7, 18 is therefore characterized by tubular line sections 6, 7 and 18 with different internal diameters. In principle, it is also possible that only the line sections 6' and 18' of the tubular line sections 6 and 18, respectively, inserted into the blood pump 10 and the substituate pump 21, have different internal diameters, while the line sections which are not lying in the pumps do not, however, differ from one another in terms of their internal diameter.

During the rinsing phase, two tubular line sections 6, 18 with different internal diameters $d_A$, $d_B$ are connected in series, with the rinsing fluid being pumped by the substituate pump 21 in the line section 18 and the fluid being pumped by the blood pump 10 in the line section 6.

Figure 3:
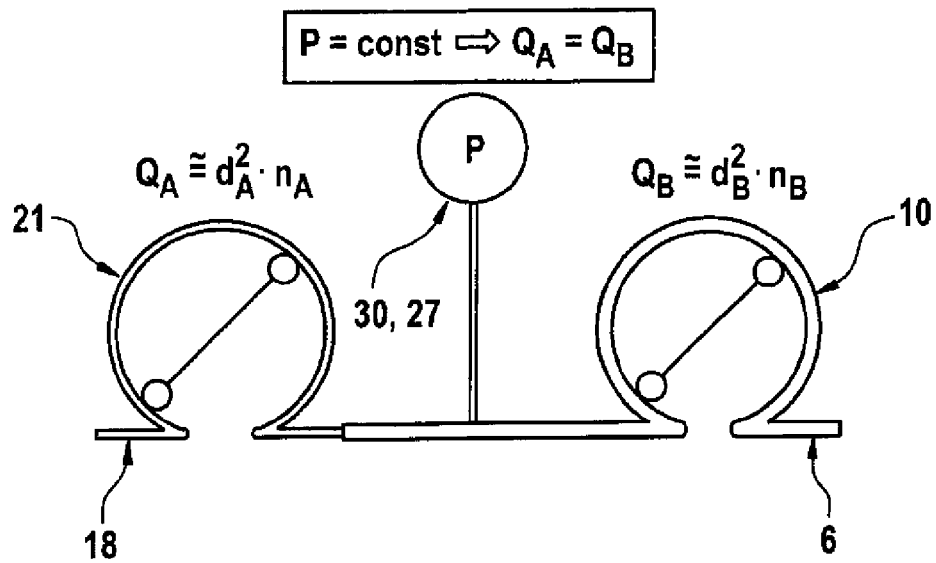
FIG. 3 shows an equivalent schematic of two tubular line sections of the tubular line system and two pumps.

FIG. 3 shows an equivalent schematic with the two tubular line sections 18, 6 and the two pumps 21, 10, as well as the pressure measuring unit 27, 30 with the pressure sensor 27 to measure the system pressure P in the tubular line section 6. The recognition of the tubular line section is effected by holding the resultant system pressure P constant and possibly readjusting the rotational speed of one of the two pumps.

The feed rate $Q_{A,B}$ of the two occluding tube pumps 21, 10, in particular roller pumps, depends on the inner tubular cross section and the displacement speed of the constriction or occlusion site of the tube pumps. The following holds for the occluding roller pump:

$$Q = V_i \cdot i \cdot n,$$

in which $V_i$ is the unit volume in ml enclosed between two rollers of the roller pump, i is the number of rollers and n is the rotor rotational speed in r.p.m. The enclosed unit volume is proportional to the square of the internal diameter d of the tubular line inserted into the pump.

Figure 4A:
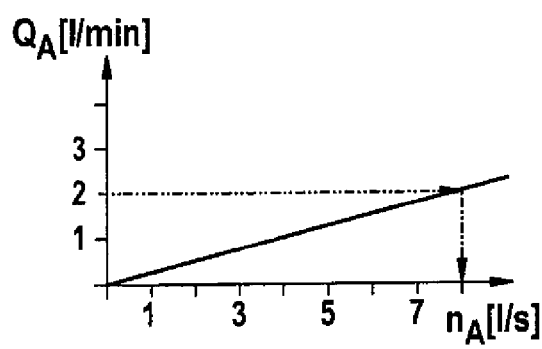
FIG. 4 shows the flow rates of the pumps from FIG. 3 as a function of the pump rotational speed.
Figure 4B:
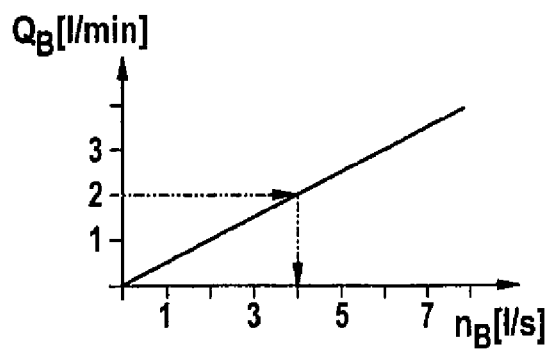

FIGS. 4A and 4B show the flow rates $Q_A$ and $Q_B$ [1/min] of the pump A (substituate pump 21) and the pump B (blood pump 6) as a function of the rotational speed $n_A$ and $n_B$ [1/s]. It can be seen that different internal diameters $d_A$, $d_B$ of the tubular lines lead to different relations between the rotational speeds $n_A$, $n_B$ of the pumps A and B. If the relation between the rotational speeds $n_A/n_B$ differ from each other at constant system pressure P, different tubular diameters are present.

Knowing the internal diameter $d_A$ or $d_B$ of the one tubular line section permits the deduction of the internal diameter $d_B$ or $d_A$ of the other tubular line section if the relation between the rotational speeds $n_A/n_B$ is calculated.

$$d_A = d_B \cdot \sqrt{\frac{n_B}{n_A}}$$

In order to recognize the tubular system, the evaluation unit 25 communicates with the central control unit 24 and receives the pressure signal of the pressure measuring unit 27, 30. First of all, the central control unit 24 initiates a connection test to ensure that the substitution fluid line 18 is connected to the arterial blood line 6 for the rinsing process. The blood pump 10 is stopped for this purpose, while the substitute pump 21 is operational. If a positive system pressure P is measured in the blood line 6 by the pressure measuring unit 27, 30, the evaluation unit deduces that both tubular line sections are connected to one another. Subsequently, the control unit 24 actuates the blood pump 10 with a constant rotational speed $n_B$. This results in a certain flow rate $Q_B$ at which the blood pump 10 pumps fluid. At the same time, the control unit actuates the substitute pump 21 with a rotational speed $n_A$, which is greater than the rotational speed $n_B$ of the blood pump 10. Here, the system pressure P is monitored by the pressure measuring unit. If both tubular line sections 18, 6 had the same internal diameter ($d_A=d_B$), a constant system pressure P could only be achieved if the rotational speeds of both pumps were equal ($n_A=n_B$). This is because only in this case do the same flow rates $Q_A=Q_B$ result when the pump rotational speeds are equal.

However, since the internal diameter $d_B$ of the tubular line of the tubular line section 6 is greater than the internal diameter $d_A$ of the tubular line of the tubular line section 18 in the present exemplary embodiment, the substitute pump 21 has to be operated at a higher rotational speed $n_A$ in order to set a constant system pressure P.

The central control unit 24 adjusts the rotational speed of the substitute pump 21 until a constant system pressure P is set in a predetermined time interval (measurement phase). As a result of the different rotational speeds of the two pumps which result when the constant system pressure is set, the evaluation unit 25 deduces that the tubular line section 18 has a smaller internal diameter $d_A$ than the tubular line section 6. Hence, the tubular line system has been recognized.

A constant system pressure is assumed in practice even if the pressure signal from the pressure measuring unit 27, 30 is superposed by pressure pulses that can be traced back to the movements of the rollers of the blood pump 10, which rollers occlude the tubular line. The evaluation unit 25 evaluating the pressure signal therefore calculates the mean value of the pressure signal from the pressure measuring unit 27, 30 in the present exemplary embodiment, with the control unit 24 actuating the blood pump 10 and the substitute pump 21 such that a constant mean pressure is set during a predetermined time interval. However, the measured pressure signal can also be evaluated using other statistical and/or signal-processing methods.

Once the tubular line system is recognized, the central control unit 24 generates a control signal, for example to undertake an intervention in the machine control. This can for example consist of only permitting a hemodialysis, but not a hemofiltration treatment (hemodialysis filtration treatment), when the tubular line system is inserted. It is however also possible to signal the recognition of the tubular line system to the treating medical practitioner by an optical and/or acoustic sign.

It is now assumed that a tubular line system is inserted whose tubular line sections have the same internal diameter. Then the readjustment of the rotational speed $n_A$ of the substitute pump 21 by the control unit 24 results in the substituate pump 21 and the blood pump 10 having the same rotational speeds $n_A=n_B$. Then the evaluation unit 25 deduces that a tubular line system with tubular line sections having different internal diameters is not inserted. By way of example, the control unit 24 can then enable a hemofiltration (hemodiafiltration) by the blood treatment apparatus.

The rotational speeds $n_A$, $n_B$ of the substitute and blood pumps 21, 10 are compared in the evaluation unit 25 by the difference of the rotational speeds $n_A-n_B$ being calculated. The value of the difference is then compared to a specified reference value. If the value of the difference is greater than the predetermined reference value, the evaluation unit deduces that the tubular line system with tubular line sections with different internal diameters is inserted. Otherwise, it is deduced that the tubular line system has tubular line sections with the same internal diameter. Instead of forming the difference between the two rotational speeds, it is also possible to form the quotient of the rotational speeds and compare the latter to a predetermined reference value. All that matters is that the two rotational speeds are put into relation to one another.

An alternative embodiment of the device for recognizing a tubular line system is described in the following text; said device makes it possible to differentiate between a tubular line system for treating an adult and for treating a child. This alternative embodiment can be implemented in the blood treatment apparatus together with the previously described embodiment, or in place of the previously described embodiment.

The evaluation unit 25 is connected to the balancing unit 13 via a line 13' so that the evaluation unit can evaluate the balancing cycles of the balancing unit. The number of cycles is a measure of the flow rate of the fluid flowing through the dialysis fluid supply line 11. Since the volumes of the balancing chambers are known, the evaluation unit can calculate the flow rate from the cycles of the balancing unit 13.

In the present exemplary embodiment, the tubular line system is provided for treating a child. All tubular line sections 6, 7, 18 have the same internal diameter d, which is smaller than the internal diameter of the tubular lines of a tubular line system for treating an adult. The evaluation unit 25 checks, particularly during the rinsing phase, whether the correct tubular line system has been inserted. To this end, the central control unit 24 actuates the substitute pump 21 with a predetermined rotational speed $n_A$. The rotational speed $n_A$, at which the substitute pump is operated, is that rotational speed which is required for setting a certain flow rate if the tubular system for children is inserted into the blood treatment apparatus. While the substitute pump 21 is operational, the evaluation unit 25 monitors the actual flow rate Q at which the substitute pump 21 draws in rinsing fluid. If the flow rate measured with the balancing unit 13 deviates from the assumed flow rate by a value which is greater than a reference value, the evaluation unit 25 deduces that it is not a tubular system for children that has been inserted into the blood treatment apparatus. However, in the present case, the correct tubular line system for children is inserted. It is for this reason that the measured flow rate is substantially equal to the assumed flow rate, i.e. the difference of both flow rates is smaller than a predetermined reference value, so that the evaluation unit deduces that a tubular system for children has been inserted. Thereupon the control unit 24 once again generates a control signal so that an intervention in the machine control can be undertaken. By way of example, certain specifications for the blood treatment which are required for treating a child can be set. However, it is also possible to signal the recognition of the tubular line system to the treating medical practitioner by an optical and/or acoustic sign.

The invention claimed is:

1. An apparatus for extracorporeal blood treatment comprising:
    a dialyser or filter having a first chamber and a second chamber separated by a semipermeable membrane;
    at least one pump to be operated at a predetermined rotational speed n for pumping fluid in a tubular line system to be inserted into the extracorporeal blood treatment apparatus; and
    a central control unit for controlling the extracorporeal blood treatment apparatus; and
    a device for recognizing the tubular line system to be inserted into the extracorporeal blood treatment apparatus comprising: an evaluation unit configured such that the tubular line system is recognized on the basic principle of the flow rate Q with which the fluid is pumped in a tubular line section of the tubular line system by the at least one pump, depending on the rotational speed n at which the at least one pump is operated, and the internal diameter d of the tubular line section.

2. The apparatus according to claim 1, wherein the evaluation unit interacts with the central control unit, the evaluation unit configured to generate a control signal for the central control unit after recognizing the tubular line system so that the control unit intervenes in the control of the extracorporeal blood treatment apparatus.

3. The apparatus according to claim 1, wherein the at least one pump is a peristaltic pump into which the tubular line section of the tubular line system is inserted.

4. The apparatus according to claim 1, wherein the at least one pump comprises: a first pump for pumping fluid in a first tubular line section of the tubular system and a second pump for pumping fluid in a second tubular line section of the tubular system, the first tubular line section and the second tubular line section being arranged one behind the other, the first tubular line section having a first internal diameter $d_A$, and the second tubular line section having a second internal diameter $d_B$; and
    the device for recognizing the tubular line system further comprises a pressure measuring unit for measuring the pressure in a tubular line section between the first pump and the second pump,
    wherein the evaluation unit is configured to interact with the control unit and the pressure measuring unit such that the evaluation unit determines the relation between the rotational speeds of the first and second pumps at which the pressure measured by the pressure measuring unit remains unchanged in a predetermined time interval,
    wherein if the rotational speed of the first pump and the second pump is different, the evaluation unit is configured to deduce that the internal diameters of the first tubular line section and the second tubular line section are different from one another, and
    wherein if the rotational speed of the first pump and the second pump is substantially the same, the evaluation unit is configured to deduce that the internal diameters of the first tubular line section and second tubular line section are equal.

5. The apparatus according to claim 4, wherein the evaluation unit interacts with the control unit and the pressure measuring unit such that:
    in a first step, the second pump is operated at a predetermined rotational speed so that, in the second tubular line section, fluid is pumped at a predetermined flow rate, and the first pump is operated at a predetermined first rotational speed which is greater than the rotational speed of the second pump, and
    in a second step, the pressure in the section of the tubular line between the first pump and the second pump is monitored and the rotational speed of the first pump is changed until a second rotational speed is reached at which the pressure in the section of the tubular line between the first pump and the second pump remains constant,
    wherein the evaluation unit is configured to deduce that the internal diameter of the first tubular line is smaller than the internal diameter of the second tubular line if the second rotational speed of the first pump is greater than the rotational speed of the second pump, and
    wherein the evaluation unit is configured to deduce that the internal diameter of the first tubular line is equal to the internal diameter of the second tubular line if the second rotational speed of the first pump is substantially equal to the rotational speed of the second pump.

6. The apparatus according to claim 1, wherein the device for recognizing the tubular line system further comprises a measuring unit for measuring the flow rate of the at least one pump in the tubular line section of the tubular line, and
    wherein the evaluation unit is configured to interact with the control unit and the measuring unit for measuring the flow rate such that the at least one pump is operated at a predetermined rotational speed at which the fluid is pumped at a certain flow rate in a determined tubular line which has a predetermined internal diameter, and that the predetermined flow rate is compared to the flow rate measured by the measuring unit for measuring the flow rate,
    wherein the evaluation unit is configured to deduce that the internal diameter of the tubular line differs from the internal diameter of the determined tubular line if the flow rate predetermined by the set rotational speed deviates from the measured flow rate by an amount which is greater than a reference value, and
    wherein the evaluation unit is configured to deduce that the internal diameter of the tubular line is equal to the internal diameter of the determined tubular line if the flow rate predetermined by the set rotational speed does not deviate from the measured flow rate by an amount which is greater than the reference value.

7. A method for recognizing a tubular line system to be inserted into an extracorporeal blood treatment apparatus, in which the extracorporeal blood treatment apparatus comprises:
    a dialyser or filter having a first chamber and a second chamber separated by a semipermeable membrane,
    at least one pump to be operated at a predetermined rotational speed n for pumping fluid in a tubular line system to be inserted into the extracorporeal blood treatment apparatus, and
    a central control unit for controlling the extracorporeal blood treatment apparatus,
    said method comprising:
    pumping, via the at least one pump operated at the predetermined rotational speed n, fluid in the tubular line system;
    measuring a flow rate Q with which the fluid is pumped;
    determining an internal diameter d of a tubular line section of the tubular line system; and recognizing the tubular line system on the basic principle of the flow rate Q with which the fluid is pumped in the tubular line section of the tubular line system by the at least one pump, depending on the rotational speed n at which the at least one pump is operated, and the internal diameter d of the tubular line section.

8. The method according to claim 7, further comprising: generating a control signal for the central control unit after the tubular line system is recognized so that the control unit intervenes in the control of the blood treatment apparatus.

9. The method according to claim 7, wherein the at least one pump is a peristaltic pump into which the tubular line section of the tubular line system is inserted.

10. The method according to claim 7, wherein the at least one pump comprises: a first pump for pumping fluid in a first tubular line section, and a second pump for pumping fluid in a second tubular line section of the tubular system, the first tubular line section and the second tubular line section being arranged one behind the other, the first tubular line section having a first internal diameter, and the second tubular line section having a second internal diameter, said method further comprising:
measuring a pressure in a section of the tubular line between the first pump and the second pump;
evaluating the relation between the rotational speeds of the first pump and the second pump at which the measured pressure remains unchanged in a predetermined time interval; and
if the rotational speed of the first pump and the second pump differ, deducing that the internal diameters of the first tubular line section and second tubular line section differ from one another, and
if the rotational speed of the first pump and the second pump are substantially the same, deducing that the internal diameters of the first tubular line section and second tubular line section are equal.

11. The method according to claim 10, further comprising:
operating the second pump at a predetermined rotational speed so that fluid in the second tubular line section is pumped at a predetermined flow rate;
operating the first pump at a predetermined first rotational speed which is greater than the rotational speed of the second pump;
monitoring the pressure in the section of the tubular line between the first pump and the second pump;
changing the rotational speed of the first pump until a second rotational speed is reached at which the pressure in the section of the tubular line between the first pump and the second pump remains constant;
deducing that the internal diameter of the first tubular line is smaller than the internal diameter of the second tubular line if the second rotational speed of the first pump is greater than the rotational speed of the second pump; and
deducing that the internal diameter of the first tubular line is equal to the internal diameter of the second tubular line if the second rotational speed of the first pump is substantially equal to the rotational speed of the second pump.

12. The method according to claim 7, further comprising:
measuring the flow rate of the at least one pump in the tubular line section of the tubular line;

operating the at least one pump at a predetermined rotational speed at which the fluid is pumped at a certain flow rate in a determined tubular line which has a predetermined internal diameter;
comparing the predetermined flow rate to the measured flow rate;
deducing that the internal diameter of the tubular line differs from the internal diameter of the determined tubular line if the flow rate predetermined by the set rotational speed deviates from the measured flow rate by an amount which is greater than a reference value; and
deducing that the internal diameter of the tubular line is equal to the internal diameter of the determined tubular line if the flow rate predetermined by the set rotational speed does not deviate from the measured flow rate by an amount which is greater than the reference value.

13. A method for recognizing a tubular line system to be inserted into an extracorporeal blood treatment apparatus, in which the extracorporeal blood treatment apparatus comprises:
a dialyser or filter having a first chamber and a second chamber separated by a semipermeable membrane,
at least one pump to be operated at a predetermined rotational speed n for pumping fluid in a tubular line system to be inserted into the extracorporeal blood treatment apparatus, and
a central control unit for controlling the extracorporeal blood treatment apparatus,
said method comprising:
pumping, via the at least one pump operated at the predetermined rotational speed n, fluid in the tubular line system;
determining an internal diameter d of a tubular line section of the tubular line system; and
recognizing the tubular line system on the basic principle of the flow rate Q with which the fluid is pumped in the tubular line section of the tubular line system by the at least one pump, depending on the rotational speed n at which the at least one pump is operated, and the internal diameter d of the tubular line section,
wherein the at least one pump comprises:
a first pump for pumping fluid in a first tubular line section, and
a second pump for pumping fluid in a second tubular line section of the tubular system, the first tubular line section and the second tubular line section being arranged one behind the other, the first tubular line section having a first internal diameter, and the second tubular line section having a second internal diameter,
said method further comprising:
measuring a pressure in a section of the tubular line between the first pump and the second pump;
evaluating the relation between the rotational speeds of the first pump and the second pump at which the measured pressure remains unchanged in a predetermined time interval; and
if the rotational speed of the first pump and the second pump differ, deducing that the internal diameters of the first tubular line section and second tubular line section differ from one another, and if the rotational speed of the first pump and the second pump are substantially the same, deducing that the internal diameters of the first tubular line section and second tubular line section are equal.

* * * * *